United States Patent
Macaulay et al.

(10) Patent No.: US 7,966,057 B2
(45) Date of Patent: Jun. 21, 2011

(54) METHODS AND APPARATUS FOR GUIDED TRANSLUMINAL INTERVENTIONS USING VESSEL WALL PENETRATING CATHETERS AND OTHER APPARATUS

(75) Inventors: Patrick E. Macaulay, San Jose, CA (US); Theodore C. Lamson, Pleasanton, CA (US); Joshua Makower, Los Altos, CA (US); Isaac Han Joon Kim, San Jose, CA (US); Brian R. Beckey, Santa Clara, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 2086 days.

(21) Appl. No.: 10/467,274

(22) PCT Filed: Feb. 6, 2002

(86) PCT No.: PCT/US02/03941
§ 371 (c)(1),
(2), (4) Date: Mar. 12, 2004

(87) PCT Pub. No.: WO02/062265
PCT Pub. Date: Aug. 15, 2002

(65) Prior Publication Data
US 2004/0147837 A1     Jul. 29, 2004

Related U.S. Application Data

(60) Provisional application No. 60/266,800, filed on Feb. 6, 2001.

(51) Int. Cl.
*A61B 5/05* (2006.01)
(52) U.S. Cl. ........................ 600/424; 604/528
(58) Field of Classification Search ........... 600/407–411, 600/478, 424; 604/22, 528; 606/159, 167, 606/41, 42, 130
See application file for complete search history.

(56) References Cited

U.S. PATENT DOCUMENTS

| | | | |
|---|---|---|---|
| 5,542,915 A | | 8/1996 | Edwards et al. |
| 5,968,053 A | * | 10/1999 | Revelas ........................ 606/108 |
| 6,004,269 A | | 12/1999 | Crowley et al. |
| 6,171,303 B1 | * | 1/2001 | Ben-Haim et al. .............. 606/15 |
| 6,233,474 B1 | * | 5/2001 | Lemelson ..................... 600/411 |
| 6,253,770 B1 | * | 7/2001 | Acker et al. .................. 128/899 |
| 6,254,573 B1 | * | 7/2001 | Haim et al. ................... 604/157 |
| 6,285,898 B1 | * | 9/2001 | Ben-Haim ..................... 600/374 |
| 6,302,875 B1 | * | 10/2001 | Makower et al. .............. 604/528 |
| 6,321,109 B2 | * | 11/2001 | Ben-Haim et al. ............. 600/424 |
| 6,327,492 B1 | * | 12/2001 | Lemelson ..................... 600/434 |
| 6,332,089 B1 | | 12/2001 | Acker et al. |
| 6,400,980 B1 | * | 6/2002 | Lemelson ..................... 600/478 |

(Continued)

FOREIGN PATENT DOCUMENTS

WO    WO02/062265    8/2002

(Continued)

*Primary Examiner* — Sanjay Cattungal (57) ABSTRACT

Electro-anatomically navigated catheters (e.g., mapping catheters, tissue penetrating catheters, delivery catheters and/or sheaths) and associated methods whereby devices or substances may be delivered to specific locations within a patient's body and/or penetration tracts or passageways are formed at specific locations between anatomical structures. The catheters are equipped with sensors and a sensing field is created around the body of the patient. The sensor-equipped catheters are then inserted into the patient's body and the position of the catheter-mounted sensor(s) is/are observed on a display representing the sensing field. Apparatus may be included for propelling the catheter(s) to specific locations and/or specific rotation orientations, within the patient's body.

5 Claims, 6 Drawing Sheets

U.S. PATENT DOCUMENTS

| | | | |
|---|---|---|---|
| 6,591,129 B1 * | 7/2003 | Ben-Haim et al. | 600/424 |
| 6,592,526 B1 * | 7/2003 | Lenker | 600/463 |
| 6,702,777 B2 * | 3/2004 | Haim et al. | 604/66 |
| 6,751,492 B2 * | 6/2004 | Ben-Haim | 600/374 |
| 6,788,967 B2 * | 9/2004 | Ben-Haim et al. | 600/424 |
| 6,915,149 B2 * | 7/2005 | Ben-Haim | 600/374 |
| 7,306,593 B2 * | 12/2007 | Keidar et al. | 606/34 |
| 7,384,411 B1 * | 6/2008 | Condado | 604/96.01 |
| 2001/0003790 A1 * | 6/2001 | Ben-Haim et al. | 600/424 |
| 2002/0013615 A1 * | 1/2002 | Haim et al. | 607/120 |
| 2002/0045809 A1 * | 4/2002 | Ben-Haim | 600/374 |
| 2002/0165448 A1 * | 11/2002 | Ben-Haim et al. | 600/424 |
| 2003/0125615 A1 * | 7/2003 | Schwartz | 600/374 |
| 2003/0129750 A1 * | 7/2003 | Schwartz | 435/377 |
| 2004/0059280 A1 | 3/2004 | Makower et al. | |
| 2004/0147837 A1 * | 7/2004 | Macaulay et al. | 600/424 |
| 2006/0079740 A1 * | 4/2006 | Silver et al. | 600/309 |
| 2009/0216125 A1 * | 8/2009 | Lenker | 600/445 |
| 2010/0210938 A1 * | 8/2010 | Verard et al. | 600/424 |

FOREIGN PATENT DOCUMENTS

WO  WO2004/068947  8/2004

\* cited by examiner

METHODS AND APPARATUS FOR GUIDED TRANSLUMINAL INTERVENTIONS USING VESSEL WALL PENETRATING CATHETERS AND OTHER APPARATUS

RELATED APPLICATIONS

This application is the United States national stage under 35 U.S.C. 371 of PCT International Application No. PCT/US2002/03941, filed Feb. 6, 2002, which in turn claims priority to U.S. Provisional Patent Application No. 60/266,800 filed Feb. 6, 2001.

FIELD OF THE INVENTION

The invention pertains generally to the fields of medicine and medical devices and more particularly to methods and devices for performing image-guided procedures within a subject's body.

BACKGROUND

The prior art has included a number of electro-anatomical methods and apparatus for anatomical mapping of portions of a patient's body and/or for determining the position and rotational orientation of a catheter or probe within the patient's body. Examples of such prior art devices and methods include those described in U.S. Pat. Nos. 5,647,361; 5,820,568; 5,730,128; 5,722,401; 5,578,007; 5,558,073; 5,465,717; 5,568,809; 5,694,945; 5,713,946; 5,729,129; 5,752,513; 5,833,608; 5,935,061; 5,931,818; 6,171,303; 5,931,818; 5,343,865; 5,425,370; 5,669,388; 6,015,414; 6,148,823 and 6,176,829.

SUMMARY OF THE INVENTION

In accordance with the present invention, there are provided a) vessel wall penetrating catheters and apparatus that are passable through or used in conjunction with vessel wall penetrating catheters, b) catheters useable to deliver radially expandable apparatus (e.g., connectors, stents, stent-grafts, occlusive blockers, etc.), c) other devices useable to perform the PICVA, PICAB, substance delivery or any of the other procedures disclosed and claimed in U.S. Pat. Nos. 5,830,222, 6,068,638 and 6,071,292 or copending U.S. patent application Ser. Nos. 08/730,327, 09/056,589, 09/282,276 and 09/282,774, equipped with sensors that are useable in conjunction with other extracorporeally located apparatus to guide the three-dimensional positioning and/or rotational orientation of such catheters and devices within the bodies of human or animal patients. Additionally, there are provided methods of using these sensor-equipped catheters to penetrate from a location within the lumen of a blood vessel or other anatomical structure to a target location (e.g., the lumen of another blood vessel or luminal anatomical structure, other locations on the same blood vessel or luminal anatomical structure, a tumor, an aberrant anatomical structure or malformation, site(s) at which drugs or other substances are to be deposited, site(s) at which apparatus (e.g., electrodes, sensors, etc.) are to be deposited, and/or site(s) from which tissue or fluid (e.g., tissue biopsies, blood samples, other body fluid samples, ova, etc) are to be harvested or obtained).

Further in accordance with this invention, there is provided a sensor-equipped vessel wall penetrating catheter device that generally comprises a) a catheter, b) a penetrator that is advanceable from the catheter to penetrate outwardly through the wall of a vessel or anatomical conduit in which the catheter is positioned and to a target location and c) at least one sensor mounted on or in the catheter. These sensor-equipped vessel wall penetrating catheters are inserted into the body of a patient and one or more energy-field-creating apparatus (e.g., magnet(s), ultrasound generator(s), light source(s), radiofrequency generator(s), x-ray machine(s), infrared source(s), microcurrent source(s), etc.)) are used to create electromagnetic fields or other energy field (i.e. "Sensing fields") around and/or within the patient's body. A sensor-monitoring and indicia-providing means (e.g., a computer controller and monitor) is then used to receive signals from the sensor(s) and to provide, on the basis of those signals, indicia of the position and/or rotational orientation of each sensor within the sensing field. In some applications, the specific anatomy of all or a portion of the patients body may be mapped using known techniques such as tomographic imaging techniques. Such anatomical mapping data is provided to a computer along with signal(s) received from the sensor(s) mounted on or in the vessel wall penetrating catheter. The computer is programmed to determine the precise location and/or orientation of the sensor(s) within the anatomically mapped region(s) of the patient's body, using the anatomical mapping data and sensor signals provided to the computer. In this manner, the sensor-equipped vessel wall penetrating catheter may be inserted into the patient's body and advanced into an anatomically-mapped area of interest. The electromagnetic field(s) or other energy is then actuated and the signal(s) from the catheter-mounted sensor(s) is/are received by the computer. The computer then provides an image or other indication of the precise longitudinal position and rotational orientation of the sensor-equipped vessel wall penetrating catheter, within the patient's body. In this manner the catheter may be precisely positioned and rotationally oriented so that, when the penetrator is advanced from the catheter, the penetrator will penetrate to the intended target location. Specific examples of sensors, sensor-monitoring and indicia-providing means (including and in addition to the computer) and energy-field creating apparatus and related software and methodology useable in this invention are described in U.S. Pat. No. 5,833,608 (Acker) entitled "Magnetic Determination of Position and Orientation as well as other U.S. Pat. Nos. 5,647,361; 5,820,568; 5,730,128; 5,722,401; 5,578,007, 5,558,073; 5,465,717; 5,568,809; 5,694,945; 5,713,946; 5,729,129; 5,752,513; 5,833,608; 5,935,061; 5,931,818; 6,171,303; 5,931,818; 5,343,865; 5,425,370; 5,669,388; 6,015,414; 6,148,823 and 6,176,829, the entireties of which are expressly incorporated herein by reference.

Further in accordance with this invention, there are provided methods wherein the above-summarized sensor-equipped vessel wall penetrating catheter is used to penetrate from a position within the lumen of a blood vessel, other type of luminal anatomical structure or conduit (e.g., ureter, fallopian tube), outwardly through the wall of the vessel or conduit in which the vessel-wall penetrating catheter is positioned, and to a target location (e.g., another blood vessel or luminal anatomical structure, other locations on the same blood vessel or luminal anatomical structure, tumors, aberrant anatomical structures or malformations, site(s) at which drugs or other substances are to be deposited, site(s) at which apparatus (e.g., electrodes, sensors, etc.) are to be deposited, and/or sites from which tissue or fluid (e.g., tissue biopsies, blood samples, other body fluid samples, ova, etc) are to be harvested or obtained).

Further in accordance with this invention, there is provided a sensor-equipped delivery catheter for navigated delivery of a radially expandable implantable device, such as a stent, a stent-graft, a tube graft, an embolic blocker such as those described in U.S. patent application Ser. Nos. 08/730,327, 09/117,516 and 09/613,675 the entireties of which are expressly incorporated herein by reference or a connector device useable for connecting two blood vessels in which openings have been formed, as described in U.S. patent application Ser. Nos. 08/730,327; 09/117,515; 09/117,520; 09/267,943; 08/868,307 and 08/970,694, the entireties of which are expressly incorporated herein by reference. These sensor-equipped delivery catheters of the present invention generally comprise a) a catheter, b) a radially expandable implantable device mounted on or in the catheter and c) at least one sensor mounted on or in the catheter. These sensor-equipped delivery catheters are inserted into the body of a patient and one or more energy-field-creating apparatus (e.g., magnet(s), ultrasound generator(s), light source(s), radiofrequency generator(s), x-ray machine(s), etc.)) are used to create electromagnetic fields or other energy field (i.e. "sensing fields") around and/or within the patient's body. A sensor-monitoring and indicia-providing means (e.g., a computer/controller and monitor) is then used to receive signals from the sensor(s) and to provide, on the basis of those signals, indicia of the position and/or rotational orientation of each sensor within the sensing field. In some applications, the specific anatomy of all or a portion of the patients body may be mapped using known techniques such as tomographic imaging techniques. Such anatomical mapping data is provided to a computer along with signal(s) received from the sensor(s) mounted on or in the vessel wall penetrating catheter. The computer is programmed to determine the precise location and/or orientation of the sensor(s) within the anatomically mapped region(s) of the patient's body, using the anatomical mapping data and sensor signals provided to the computer. In this manner, the sensor-equipped delivery catheter may be inserted into the patient's body and advanced into an anatomically-mapped area of interest. The electromagnetic field(s) or other sensing field is then actuated and the signal(s) from the catheter-mounted sensor(s) is/are received by the computer. The computer then provides an image or other indication of the precise longitudinal position and rotational orientation of the sensor-equipped delivery catheter, within the patient's body. In this manner, the operator may precisely position and rotationally orient the delivery catheter so that subsequent deployment and release of the radially expandable implantable device from the catheter will result in implantation of the device at the intended implantation site and/or in an intended rotational orientation. Specific examples of sensors, sensor-monitoring and indicia-providing means (including and in addition to the computer) and energy-field creating apparatus and related software and methodology useable in this invention are described in U.S. Pat. No. 5,833,608 (Acker) entitled "Magnetic Determination of Position and Orientation as well as other U.S. Pat. Nos. 5,647,361; 5,820,568; 5,730,128; 5,722,401; 5,578,007; 5,558,073; 5,465,717; 5,568,809; 5,694,945; 5,713,946; 5,729,129; 5,752,513; 5,833,608; 5,935,061; 5,931,818; 6,171,303; 5,931,818; 5,343,865; 5,425,370; 5,669,388; 6,015,414; 6,148,823 and 6,176,829, the entireties of which are expressly incorporated herein by reference.

Further in accordance with this invention, there are provided methods wherein the above-summarized sensor-equipped delivery catheter is used to deliver a radially expandable implantable device to a specific location and in a specific rotational orientation within a human or veterinary patient's body.

Still further in accordance with the invention, the "sensing field" may further operate as a propulsion field whereby certain components of the field are controlled in a manner that propels or moves a sensor-equipped vessel penetrating catheter, a sensor equipped delivery catheter, an accompanying guidewire and/or portions thereof (e.g., the penetrator of the vessel wall penetrating catheter) through the patient's body to a specific target site and/or in specific rotational orientation(s).

Still further in accordance with the invention, the sensor(s) mounted on or in the above-summarized vessel penetrating catheter and/or delivery catheter may be replaced by, or may function as an emitter or transmitter rather than a sensing and the sensing field generating apparatus maybe replaced by apparatus for detecting those transmitter(s) or receiver(s). Such detecting apparatus may be positioned at several locations around or in the patient's body such that the precise 3 dimensional position and/or rotational orientation of each catheter-mounted emitter or transmitter may be computed.

Further objects, aspects and elements of this invention will be apparent to those of skill in the art upon reading and understanding the detailed description and examples set forth herebelow and in the accompanying drawings and/or appended documents.

BRIEF DESCRIPTION OF THE DRAWINGS

FIG. 3a' is a cross sectional view through line 3a'-3a' of FIG. 3a.

DETAILED DESCRIPTION OF EXEMPLARY EMBODIMENTS

In some embodiments, electromagnetic fields may be used to accomplish the desired catheter guidance and anatomical mapping. One example of an electromagnetic catheter guidance and positioning system that may be incorporated into the present invention is the Carto™ or NOGA™ system available from Biosense-Webster, Inc., a Johnson & Johnson Company, Diamond Bar, Calif. and described in a number of patents, including U.S. Pat. No. 5,833,608 (Acker) entitled "Magnetic Determination of Position and Orientation. In these systems, magnet(s) (e.g., electromagnetic coils) are positioned and used to generate a plurality of different magnetic fields around the patient. Each magnet has at least one non-zero component of known magnitude which is quasilinear (i.e., constant, linear, or nearly linear) with respect to distance in a certain reference direction and within a sensing volume. A controller, such as a microprocessor or computer, is connected to the magnet(s) and is operative to actuate the magnet(s) in a fashion that generates different magnetic fields in a preselected sequence. At least one sensor is mounted in a fixed position on or in the catheter (tissue penetrating catheter or catheter for delivering radially expandable blocker, connector, stent, stent-graft, etc) and the catheter is moved within the sensing volume (e.g., an anatomical region wherein the sensing is to be conducted). The catheter-mounted sensor(s) may be very small in size and preferably are of solid-state design. Each sensor detects magnetic field components in at least two different, preferably orthogonal, local directions relative to that sensor. Desirably, the sensor(s) is/are arranged to detect magnetic field components in three different, desirably orthogonal, local directions relative to the sensor(s) so as to determine the position of the catheter in three dimensions. These local directions are directions in the frame of reference of the sensor, and may differ from the reference directions of the magnet(s) used to create the magnetic field(s) around the patient's body. A calculator device, such as a computer, receives signals or other indicia of the magnetic field components detected by each sensor. This calculator device then computes the position and/or rotational orientation of each sensor relative to the magnet(s) on the basis of the magnetic field components that are detected by the sensor(s), while the magnets are operated to generate the various magnetic fields. Because the fields within the sensing volume are quasilinear, as defined above, measurable magnetic fields and rates of variation in field component magnitudes per unit distance can be determined throughout a relatively large sensing volume (e.g., a volume having dimensions of about 30 cm or more) even in instances where the maximum field is relatively low. In this manner, the apparatus can accurately monitor the rotational orientation and position of the sensor-equipped catheter as it is inserted or advanced into the body of a human or animal patient.

In many applications, the magnet(s) will generate a) a first substantially uniform magnetic field in a first reference direction within a sensing volume and b) at least a second substantially uniform magnetic field in another reference direction within the sensing volume (e.g., a "second" reference direction that is different from the first reference direction). Preferably, the second reference direction is orthogonal to the first reference direction. The magnet(s) may also generate gradient fields within the sensing volume (e.g., first and second gradient fields), such gradient fields having differing predetermined patterns of variation in the different reference directions (e.g., first and second reference directions) within the sensing volume.

Preferably, the magnet(s) may also be operable to generate a field such that a component of the field varies with a predetermined pattern of variation in a third reference direction, different from, and preferably orthogonal to, the first and second reference directions, and the calculator apparatus is arranged or programmed to determine the position of the sensor-equipped catheter in the third direction, as well as in the first and second directions. The component varying in the third direction may be provided as a part of a third gradient field different from the first and second gradient fields and from the uniform fields. Alternatively, the component varying in the third direction may be provided in the first gradient field, second gradient field or both. The magnet(s) may also be arranged to generate a third uniform field in the third reference direction.

Also, the magnets may be employed in sets, each such set including a pair of field-directing elements disposed on opposite sides of the sensing volume. The field-directing elements may be arranged to direct flux codirectionally with one another to provide a substantially uniform field in the sensing volume and to direct flux counter-directionally to one another to provide a gradient field in the sensing volume. The field-directing elements of each such pair desirably are electrically conductive coils, most preferably Helmholtz coils disposed substantially coaxially with one another so that the axis of each such pair extends in one of the reference directions.

Apparatus according to a further aspect of the invention includes a magnet structure including at least one, and in some embodiments preferably two, pair(s) of Helmholtz coils, the coils of each such pair being substantially coaxial with one another and defining a pair axis. The coils of each such pair are disposed on opposite sides of a sensing volume so that the coil axes of the various pairs are substantially orthogonal to one another. The apparatus further includes a controller (e.g., a microprocesser controller or computer) which sends actuation signals to actuate each pair of Helmholtz coils. Such actuation results in a homogeneous-field state with codirectional current flow around the pair axis in both coils of the pair to thereby generate a magnetic field directed parallel to the axis of that pair, such magnetic field having substantially uniform strength within the sensing volume. The controller may also be operative to actuate each pair of Helmholtz coils in a gradient field state with counterdirectional current flow in the coils of the pair, thereby resulting in a magnetic field that has a component directed parallel to the axis of the pair, such magnetic field component having a substantially linear gradient of magnitude in the sensing volume. The controller may be operative to cause the pairs of coils to be actuated to different states according to a preselected time sequence, typically with only one pair actuated to only one state at any given time. Apparatus according to this aspect of the invention preferably also include a sensor-equipped catheter of the present invention that is moveable within the sensing volume (e.g., within the patient's thorax), the catheter-mounted sensor being capable of measuring magnetic field components in at least two, and preferably three, mutually orthogonal local directions relative to the sensor. In this way, the catheter-mounted sensor can measure homogeneous-field local components in the local directions while the coil pairs are in the aforementioned homogeneous-field states while also measuring gradient-field local components in the local directions relative to the sensor while the coil pairs are in the aforementioned gradient field states.

The apparatus may further include apparatus for displaying an image of a portion of the patient's body (e.g., the sensing volume) obtained by an imaging technique (e.g., a tomographically generated CT image through the patient's heart or thorax) on a monitor or display along with a representation of the sensor-equipped catheter superposed thereon. The monitor display may further be adapted to accept and display body image data representing the body image in a body image frame of reference different from the frame of reference defined by the reference directions of the magnet means and/or relationship data representing the relationship between the body image frame of reference and the magnet means frame of reference. The system may further be adapted to transform the position of the sensor-equipped catheter within the magnet's frame of reference, the body image data or both, so as to provide the catheter position data and the body image data in a common frame of reference. The apparatus may also incorporate one or more fiducial markers, and means for attaching each such fiducial marker to the patient's body so that the above described superimposed images may include an image of each fiducial marker. The apparatus may further include apparatus for determining the position of each fiducial marker in the magnet's frame of reference. In this regard, each fiducial marker may include a sensor for measuring the magnetic field components, and the calculator apparatus may be arranged or programmed to determine the position and orientation of each fiducial marker from the magnetic fields measured by the sensors of the fiducial markers. In such embodiments, the relationship data may include data regarding the difference, if any, between the position and orientation of each fiducial marker as derived from magnetic field measurements and the position and orientation of the fiducial marker as shown in the image data.

The system is capable of determining not only the three-dimensional position, but also the rotational orientation, of each catheter-mounted sensor located within a patient's body. To detect the rotational orientation of a particular sensor, a plurality of magnetic fields are generated, each including one or more quasilinear components as discussed above. Desirably, the plural magnetic fields include first and second homogeneous magnetic fields, each of which has a non-zero component of substantially uniform magnitude throughout the sensing volume in first and second reference directions and further includes first and second gradient fields having components which vary in predetermined patterns of variation. As discussed above in connection with the apparatus, a sensor disposed within the sensing volume measures magnetic field components in at least two, and preferably three, different local directions relative to the sensor during application of each of these fields. In this manner, the specific rotational orientation of the catheter relative to the reference directions of the homogeneous-fields is determined from the homogeneous-field local components measured by the sensor during application of the homogeneous fields. Additionally, the position of the catheter in the reference directions (i.e., a three-dimensional determination when three reference directions are provided) is determined from the homogeneous field local components and from the gradient field local components measured during application of the first and second gradient fields.

Prior to or during the procedure, the generation of all fields by the magnet(s) may be stopped one or more times and, while such magnetic field generation is stopped, the catheter-mounted sensor(s) may be actuated to detect baseline magnetic field components, such as from the earth's magnetic field, stray magnetic sources and the like. This baseline magnetic field component data can then be used to correct the magnetic field component data acquired by the catheter-mounted sensors during the procedure. In some applications, an image of the sensor-equipped catheter may be superposed on a standard or cross-sectional anatomical image, such as an image obtained by X-ray, MRI or CT scan.

In some applications, it may be desired to place sensor(s) at target anatomical location(s) within the mapped anatomy of the patient, in addition to the provision of sensor(s) mounted on the operative catheter. In this manner, the electro-anatomical mapping and guidance system may be used to guide the precise positioning of the operative catheter-mounted sensor(s) relative to the target sensor(s). As described more fully herebelow, the use of one or more target sensor(s) in addition to the sensor(s) mounted on the operative catheter may be particularly useful when it is desired to advance a penetrator or other member from an operative catheter positioned in a relatively stable anatomical structure (e.g., the internal mammary artery or aorta) to a target site located on an anatomical structure that is moving (e.g., a coronary artery or coronary vein located on the beating heart).

A further aspect of the invention provides a method of depicting, on a monitor screen or display, the precise position and/or rotational orientation of a sensor-equipped catheter of the present invention within a previously imaged or mapped anatomical region of the patient's body. Methods according to this aspect of the invention include the steps of providing a sensor in a substantially fixed position relative to the catheter and acquiring an image of the catheter while the catheter is in a first orientation. The method further includes the step of monitoring the orientation of the sensor-equipped catheter by monitoring magnetic fields transmitted to or from the sensor-equipped catheter, to thereby monitor the orientation of the catheter when the catheter is in a moved orientation different from the first orientation. The method further includes the step of transforming the image of the catheter in the first orientation into an image of the catheter in its moved orientation and displaying the transformed image. Preferably, the monitoring, transforming and displaying steps are repeated as the catheter is moved through a range of moved orientations so that a transformed image corresponding to each such moved orientation is displayed substantially in real time when the catheter is in such moved orientation.

The method may be performed with a plurality of catheters simultaneously. Thus, separate sensors may be affixed to each of a plurality of catheters, and the steps of acquiring an image of the catheter may include the step of acquiring the images of all of the catheters in respective first positions. The steps of monitoring the orientation of the sensor and determining the orientation of the catheter may include the step of monitoring the orientation of all of the sensors and determining separate moved orientations for each catheter. The step of transforming the image may include the step of transforming the image of each catheter into an image of that catheter in its respective moved orientation. The displaying step may be conducted so as to display all of the transformed images together, so that the orientations of the transformed images relative to one another correspond to the orientations of the catheters relative to one another. For example, where the catheters are the bones connected to one another at a skeletal joint, the physician can observe the transformed images of the bones, and thus observe the relative orientations of the catheters constituting the joint during a medical procedure without taking additional x-rays as the bones are moved.

Preferably, the method includes the step of determining the position of each sensor in a fixed frame of reference while the catheters are in their respective starting orientations and while the catheters are in the respective moved orientations, so that the steps of transforming and displaying the images may include the step of adjusting the positions of the displayed transformed images relative to one another to compensate for relative movement of the catheters. Thus, the displayed images will correctly represent the positions of the catheters relative to one another.

Yet another aspect of the invention includes methods of mapping physiologic variables within the body of a living subject. A method according to this aspect of the invention desirably includes the steps of placing a sensor-equipped catheter in or on the body, sensing a physiologic variable by way of a transducer element located on the catheter and determining the position of the catheter by monitoring magnetic fields directed to or from a magnetic field sensor on the sensor-equipped catheter to thereby provide a measurement of the physiologic variable associated with a position. Most preferably, methods according to this aspect of the invention include the further steps of repeating the aforesaid steps to provide a plurality of measurements associated with a plurality of positions, to thereby provide a map of the physiologic variable over a plurality of positions. The method may further include the step of displaying such map as a visible image as, for example, as a set of contour lines, areas of different color or areas of differing contrast, with or without other features derived from other imaging modalities. For example, a map of body temperature, oxygen level or other physiologic variable can be overlaid on an MRI, CAT or similar image.

Still further aspects of the invention provide apparatus for generating one or more magnetic fields in a field frame of reference so that at least one of those magnetic fields includes at least one non-zero parameter, such non-zero parameter being quasilinear with respect to distance from point to point within the field frame of reference. The apparatus according to this aspect of the invention may further comprise a catheter adapted for disposition within the patient's body, a sensor mounted on that catheter for monitoring the magnetic field prevailing at the sensor-equipped catheter while the sensor-equipped catheter is disposed in the patient's body and for sending a signal representing at least one parameter of the so-monitored field. Additionally, there may be included a calculator apparatus for determining the position of the sensor-equipped catheter in the field frame of reference from the signal provided by the field sensor. The apparatus may also be capable of displaying an image of the patient's body along with a superimposed representation of the catheter so that the representation of the catheter appears on the displayed image at a location on the body image that conforms to the catheter position data provided by the calculator apparatus. Still further aspects of the invention include methods of operating the sensor-equipped vessel wall penetrating catheter, the sensor equipped delivery catheter for radially expandable apparatus and the other apparatus energy field generating and controlling apparatus (e.g., magnets, computer, calculator, controller, monitor/display) to accomplish navigated positioning and orientation of the sensor equipped catheter(s) within the patient's body. Specific examples of revascularization methods that use this invention are shown in FIGS. 1,4,6,7 and 8 and are fully described herebelow.

Figure 5:
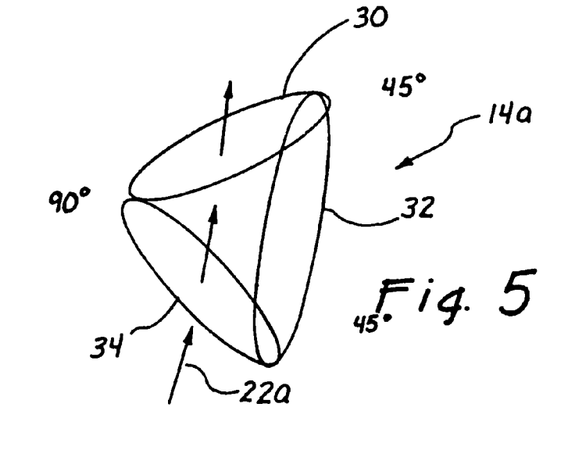
FIG. 5 is a schematic diagram of a sensor that comprises first, second and third electromagnetic coils arranged in a generally triangular configuration.

In embodiments where electromagnetic fields are used, the sensor(s) mounted on or in the catheter(s) may comprise a sheetlike support and a plurality of magnetically sensitive elements, each having a preselected sensitive direction, disposed on the support. The support may be folded so that the magnetically sensitive elements are non-coplanar. The support may incorporate a rectangular or square central panel with two side panels, a tip panel and an elongated strip all extending from different edges of the central panel to form a generally cruciform shape. The sensitive elements may be mounted on the various panels, and the panels may be folded over a dielectric core. The sensor most preferably incorporates a physiologic sensing element sensitive to a physiologic variable, this sensing element being attached to the same support as the magnetically sensitive elements. One specific sensor design that is particularly useful for over-the-wire type catheters is shown in FIG. 5 and described fully herebelow.

Referring now to the accompanying FIGS. 1-11, there are shown specific embodiments of the invention which serve as examples of the present inventive concept.

Figure 1:
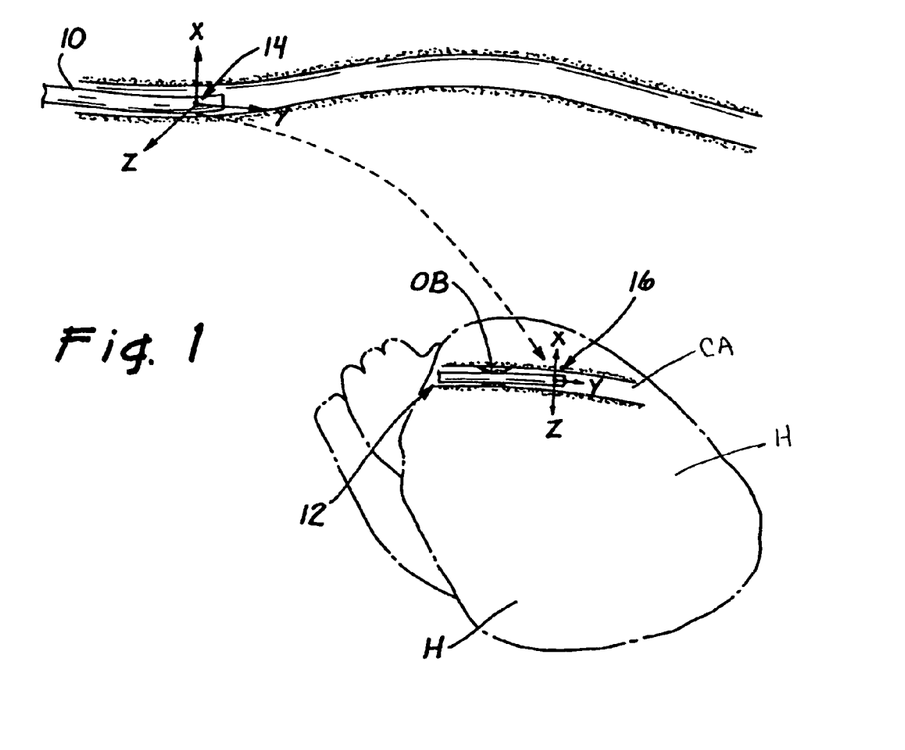
FIG. 1 is a schematic diagram of a method of the present invention where a sensor-equipped vessel wall penetrating catheter and a sensor-equipped mapping catheter are used to perform a percutaneous, catheter-based, coronary artery bypass procedure in which a tubular graft is placed between the left internal mammary artery LIMA and an obstructed coronary artery.

Procedures Using a Sensor-Equipped Mapping Catheter and a Sensor Equipped Tissue Penetrating Catheter FIG. 1 illustrates a method for using a vessel wall penetrating catheter 10 that is equipped with a magnetic field component sensor 14 and a mapping catheter 12 that is also equipped with a magnetic field component sensor 16, to perform a percutaneous, catheter-based, coronary artery bypass procedure wherein a tubular graft is placed between the left internal mammary artery LIMA and an obstructed coronary artery, distal to an obstruction OB, thereby allowing arterial blood from the LIMA to flow into the coronary artery, distal to the obstruction OB.

In this example, a preliminary tomographic scan or imaging study need not have been performed because two (2) separate sensors 14, 16 are employed to accomplish real-time, continuous sensing of the precise positions of both the vessel wall penetrating catheter 10 positioned in the LIMA and the mapping catheter 16 positioned in the obstructed coronary artery. Initially, electromagnetic coils are placed at positioned outside of the patient's body and are utilized to form electromagnetic fields, as described here above. The vessel wall penetrating catheter 10 incorporating a first magnetic sensor 14 is inserted into the patient's arterial vasculature and is advanced into the left internal mammary artery LIMA. The first sensor 14 is actuated as the vessel wall penetrating catheter 10 is advanced through the LIMA, thereby allowing the computer to accurately map the anatomy of the LIMA. The mapping catheter 12 is also inserted into the patient's arterial vasculature and advanced into the obstructed coronary artery and through the obstruction OB. With its magnetic sensor 16 actuated, the mapping catheter is advanced through the portion of the coronary artery distal to the obstruction, thereby providing to the computer accurate mapping data of the coronary artery. The computer then displays on a monitor screen a depiction of each blood vessel in each catheter. The three-dimensional sensor 14 of the being vessel wall penetrating catheter 10 is specifically mounted in fixed orientation relative to the direction in which gave long penetrator needle will advance out of and away from the catheter 10, as indicated by the dotted line labeled "long needle path." Also, a being sensor 16 mounted in the mapping catheter may be the positioned in the precise location in the coronary artery, distal to the obstruction OB, into which the graft is intended to enter. Thereafter, watching the monitor screen, the operator can rotate the vessel wall penetrating catheter 10 into a specific rotational orientation which ensures that, when the long penetrator needle is subsequently advanced, it will penetrate outwardly through the wall of the LIMA a that the location from which the bypass graft is intended to and the eighth, through the thoracic cavity and through the wall of the coronary artery into the lumen of the coronary artery immediately adjacent the position of the sensor 16 of the mapping catheter 12. With the catheter so positioned and oriented, the penetrator is then advanced in the above described manner and a guidewire is then advanced through a lumen of the penetrator and into the lumen of the coronary artery. The penetrator is then retracted into the vessel wall penetrating catheter 10, leaving the guidewire extending from the lumen of the LIMA, through the opening formed in the wall of the LIMA, through the thoracic cavity, through the opening formed in the wall of the coronary artery distal to the obstruction OB and into the on obstructed distal portion of the coronary artery lumen. Thereafter, the vessel wall penetrating catheter 10 may be extracted and a flexible tube graft may be advanced over the guidewire and the opposite ends of the tube graft may be attached to the LIMA and coronary artery. Arterial blood may then flow out of the lumen of the LIMA, through the opening formed in the wall of the LIMA, through the tube graft, through the opening formed in the wall of the coronary artery and into the lumen of the coronary artery distal to the obstruction OB, thereby accomplishing the desired bypass of the coronary artery obstruction OB.

Sensor Equipped Catheters

Figures 9, 10, 11:
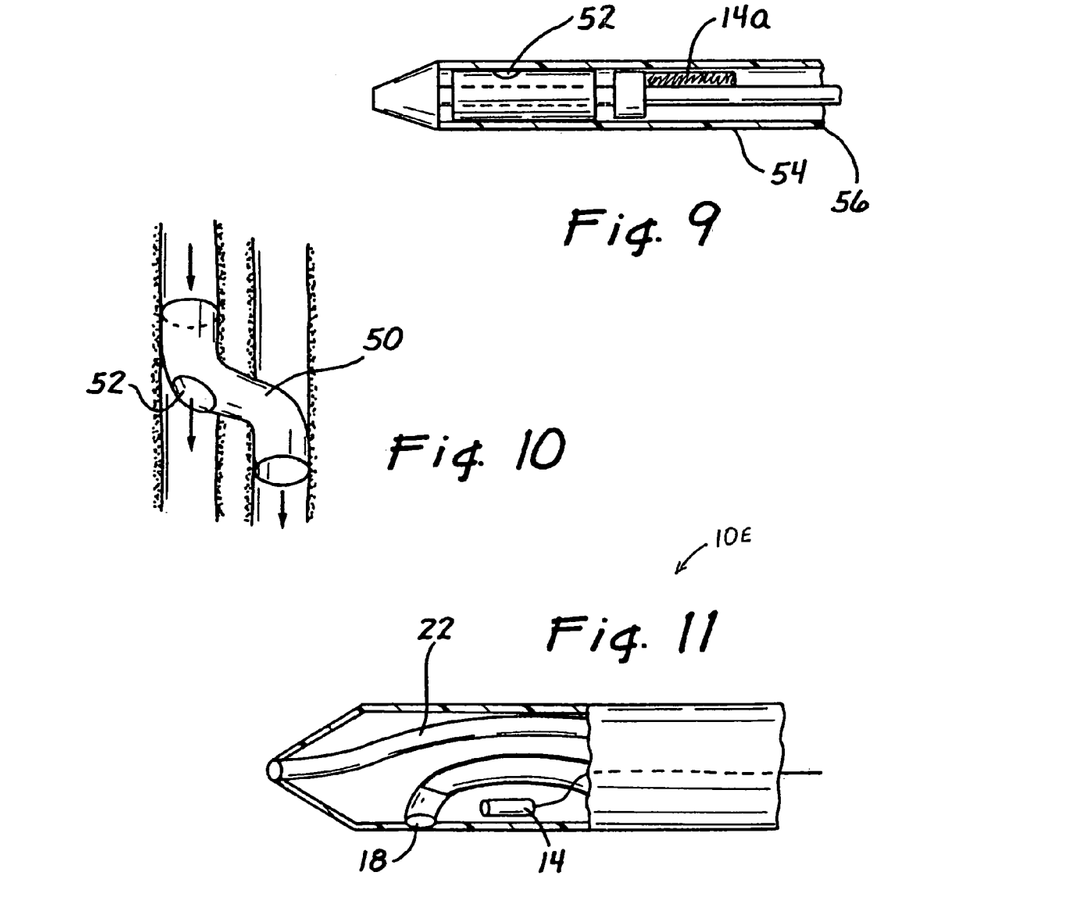
FIG. 9 is a partial sectional view of a sensor-equipped connector deliver catheter of this invention with a radially expandable connector device positioned within the delivery catheter.
FIG. 10 is a diagram of two adjacent blood vessels having a bloodflow passageway formed therebetween and a partially covered, flow-directing connector device implanted by the sensor-equipped sensor delivery catheter of FIG. 9.
FIG. 11 is a partial cut-away view of an embodiment of a sensor-equipped tissue penetrating catheter according to this invention.

FIGS. 2, 2a, 3, 3a, 3a', 3b and 11 show details of the construction of an exemplary sensor-equipped mapping catheter 10a and an exemplary sensor-equipped vessel wall penetrating catheters 10b, 10c, 10d, 10e. The vessel wall penetrating catheter 10b, 10c, 10d, 10e may incorporate or include any or all over the elements of the vessel wall catheters described in U.S. Pat. No. 5,830,222; 6,068,638; 6,159,225 or 6,071,292 or in co-pending U.S. patent application Ser. Nos. 08/730,324; 09/117,515; 08/837,295; 09/059,532; 08/837,294, 09/056,589; 09/282,276; 09/282,774; 09/507,139; 09/505,149 and/or 09/766,502, the entirety of each such patent and patent application being expressly incorporated herein by reference. Additionally, the vessel wall penetrating catheter 10b, 10c, 10d, 10e comprises a magnetic field component sensor 14 stick simply mounted on the catheter body and at a specific longitudinal location and in specific rotational or radial relationship to be outlet opening 18 and through which the penetrator 20 exits the catheter body. This magnetic field component sensor 14 preferably comprises a plurality are of magnetic coils arranged in orthogonal relationship to one another. which is expressly incorporated herein by reference. In embodiments where the vessel wall penetrating catheter 10b, 10c, 10d, 10e is desired to have a guidewire lumen 22 as shown in FIG. 11, the guidewire lumen 22 may pass through the catheter body adjacent to or side-by-side with the sensor 14, as shown in FIG. 11. However, it in other embodiments it may be desirable for the guidewire lumen to pass longitudinally through the sensor of the catheter body and for the orthogonally positioned components of the sensor 14 to be disposed about to the guidewire lumen, as shown in FIG. 5. Specifically, FIG. 5 illustrates a sensor 14a that comprises a first 30, second 32 and third 34 electromagnetic coils. These three coils 30, 32, 34 are attached to one another in a generally triangular configuration such that the guidewire lumen 22 a passes through the sensor of to the coils and is substantially sensor within the sensor 14 a.

Figures 2, 2A, 3A:
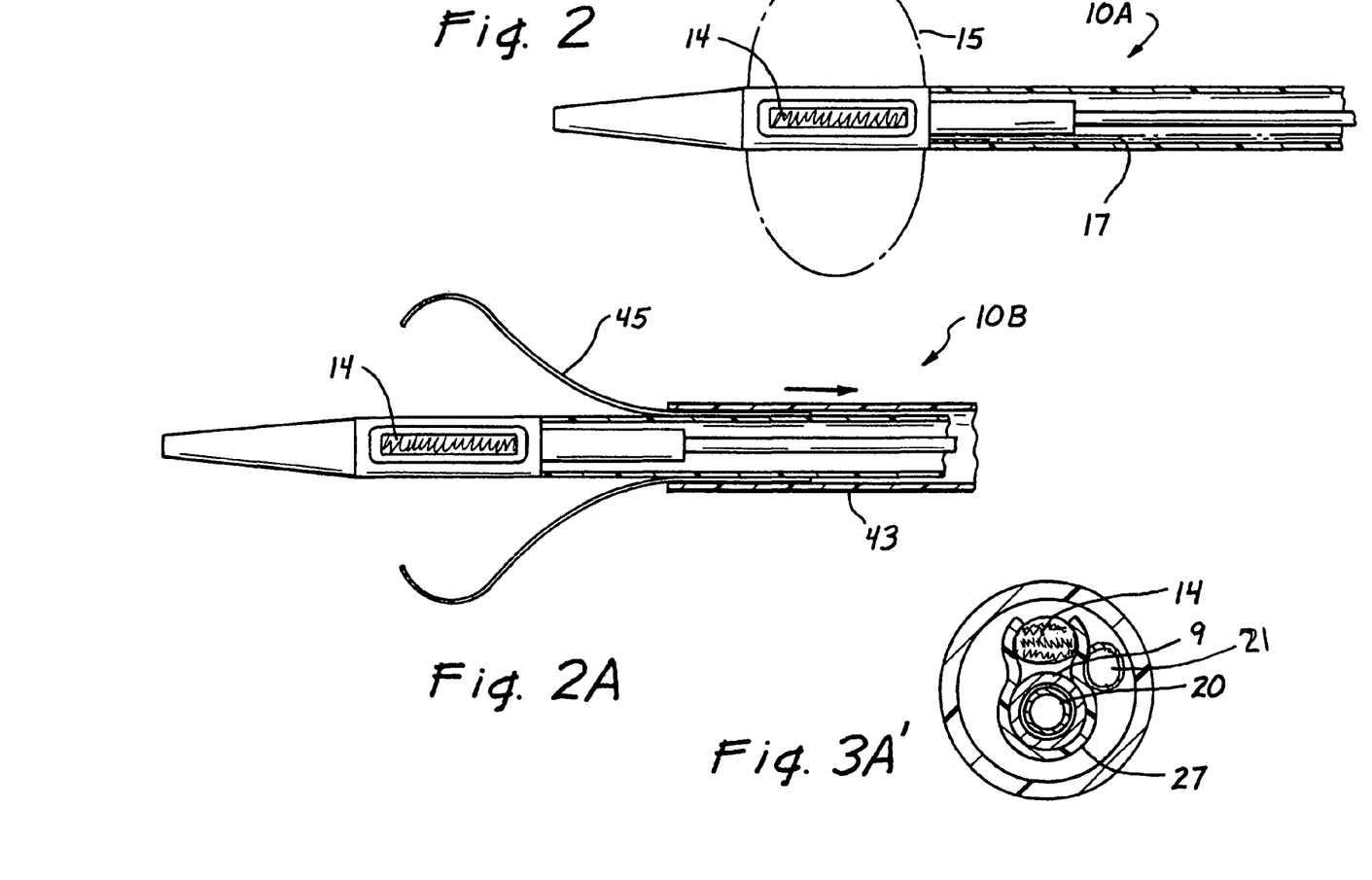
FIG. 2 is a partial, sectional view of a first embodiment of a sensor-equipped mapping catheter according to this invention.
FIG. 2a is a partial, sectional view of a second embodiment of a sensor-equipped mapping catheter according to this invention.
FIG. 3a is a partial, sectional view of a second embodiment of a sensor-equipped tissue penetrating catheter according to this invention.

FIG. 2 shows a sensor-equipped mapping catheter 10a which comprises an elongate, flexible catheter body 17 and a sensor 14 of the above described type mounted on or in the catheter body 17. An optional centering balloon 15 may be provided to center the mapping catheter 10a within the lumen of a blood vessel. Such centering of the catheter may be particularly desirable in applications were the vessel being mapped is substantially larger in diameter than the mapping catheter 10a and, thus, it is desirable to prevent the mapping catheter form undergong side-to-side movement as the mapping procedure proceeds. In embodiments where the optional centering balloon 15 is used, the balloon 15 may be inflated to a size that is close to the luminal diameter of the blood vessel but does not frictionally coapt with the blood vessel wall so firmly that the operator is prevented from longitudinally advancing or retracting the mapping catheter 10a during the mapping procedure.

FIG. 2a shows another embodiment of a mapping catheter 10b which comprises a an elongate, flexible catheter body 17 and a sensor 14 of the above described type mounted on or in the catheter body 117. A retractable sheath 43 is positioned around the catheter body 17. A plurality of centering arms 45 are attached at radially spaced apart locations around the body of the catheter 17. When the sheath 43 is advanced distally it will compress the centring arms to straight configurations and will constrain or hold the centering arms against the outer surface of the catheter body 17. When the sheath 43 is retracted, as shown in FIG. 2a, the centering arms 45 will spring outwardly and will assume their curved configurations. In this manner, the centering arms 45 will ride against the luminal wall of the vessel as the catheter 10a is advanced or retracted, thereby maintaining the sensor 14 in a substantially centered position within the vessel lumen and eliminating variability in the vessel mapping that can result form lateral or side-to-side movement of the sensor 14 within the vessel lumen.

Figure 3:
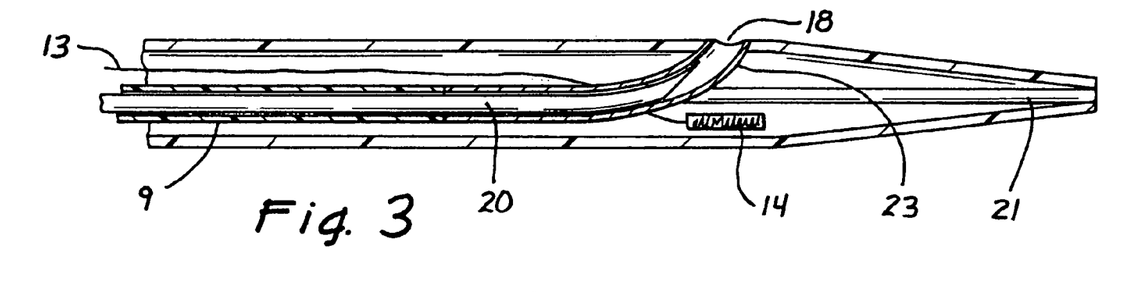
FIG. 3 is a partial, sectional view of a first embodiment of a sensor-equipped tissue penetrating catheter according to this invention.
Figure 3A:
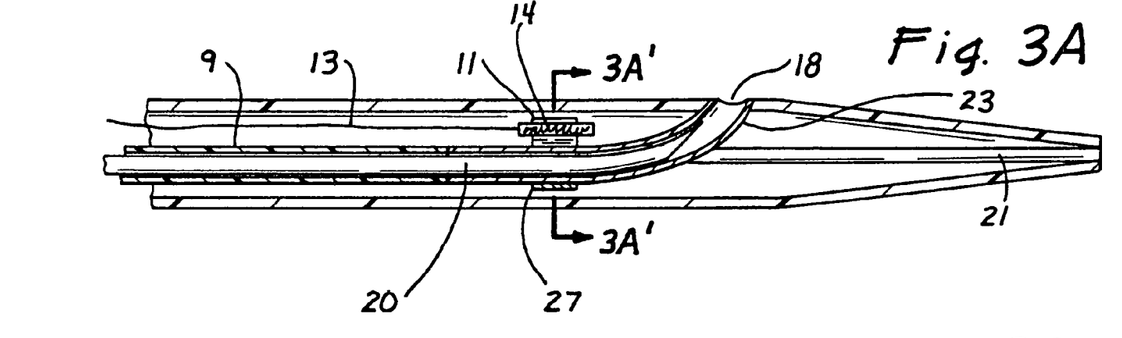
Figure 3B:
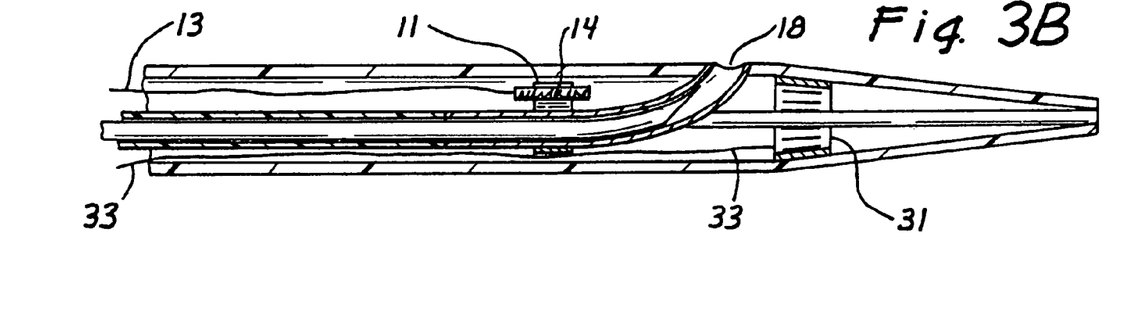
FIG. 3b is a partial, sectional view of a third embodiment of a sensor-equipped tissue penetrating catheter according to this invention, which includes an IVUS imaging transducer.

FIGS. 3-3b show several different examples of sensor-equipped tissue penetrating catheters of this invention. In the example of FIG. 3, the sensor 14 is mounted within the catheter, near the penetrator outlet aperture 18, but is not attached to the penetrator housing.

In the example of FIGS. 3a and 3a' the sensor 14 is mounted within the catheter proximal to the penetrator outlet aperture 18 and is affixed to a penetrator housing 9 by way of a stabilizer 27. The penetrator housing 9 is formed of a rigid material such as metal, and the stabilizer 27 securely attaches the sensor 14 to the housing 9. As shown in the cross sectional view of FIG. 3a', the stabilizer 27 may be specifically configured to firmly clamp or hold the sensor 14 a fixed distance from and in fixed spacial relation to the housing 9. In this manner, the stabilizer 27 prevents the sensor 14 from moving relative to the penetrator housing 27 as the catheter flexes or otherwise deforms. In this manner, the stabilizer 27 helps to ensure that the sensor will maintain a substantially constant relationship to the position of the penetrator 20 despite any flexing or bending of the catheter body as may occur in tortuous blood vessels or other curved or constricted anatomical areas.

The example of FIG. 3b incorporates the same sensor 14 and stabilizer 11 arrangement as the example shown in FIGS. 3a-3a', but further includes an imaging apparatus 31 positioned within the catheter 10d. This imaging apparatus 31 may be an intravascular ultrasound (IVUS) transducer, Doppler or any other suitable type of imaging transducer or apparatus. A wire 33 or other communication is provided to transmit image signals from the imaging apparatus 31 to a monitor located outside the patient's body. In this manner, the imaging apparatus 31 may provide an image of anatomical structures located adjacent to or near the catheter tip and such image may be used in conjunction with, merged with or superimposed upon an image of the blood vessel map or scan, such as that shown in FIG. 8 and discussed herebelow.

Example of Double CABG Procedure Performed Using Sensor-Equipped Catheters

Figure 4:
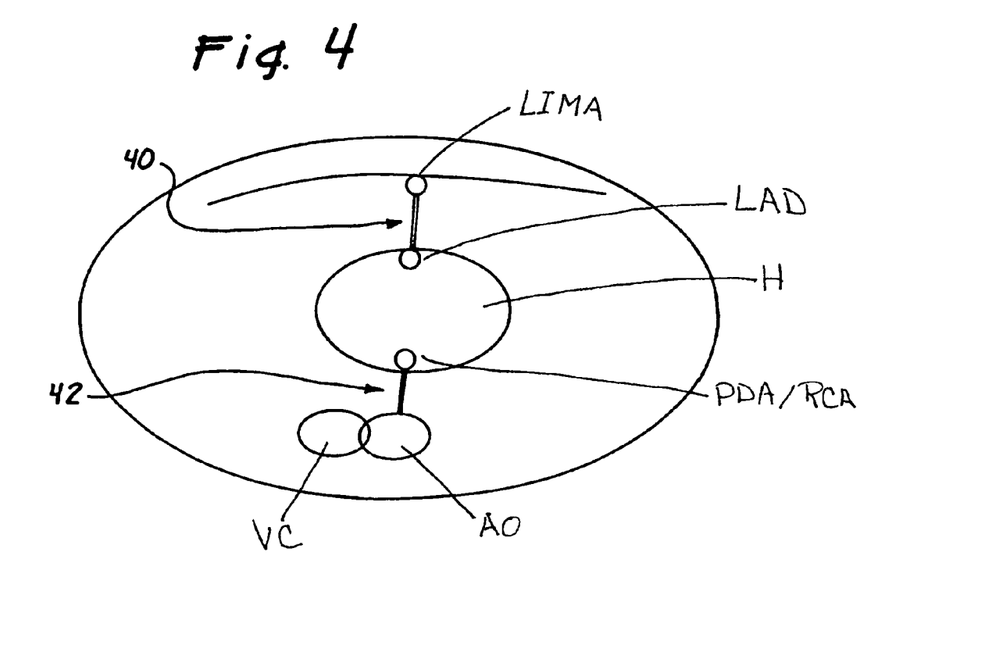
FIG. 4 is a schematic diagram of a double coronary artery bypass procedure according to this invention, wherein one tubular bypass graft is placed to connect left internal mammary artery to the left anterior descending coronary artery and a second tubular bypass graft is placed to connect the descending aorta to the right coronary artery.

FIG. 4 is a schematic illustration of a double coronary artery bypass procedure wherein one tubular bypass graft 40 connects the left internal mammary LIMA to the left anterior descending coronary artery LAD and a second tubular bypass graft 42 connects the descending aorta to the right coronary artery RCA, as shown. These tubular bypass grafts 40, 42 are installed by a percutaneous catheter based procedure as described here above and generally illustrated in FIG. 1.

The sensory-equipped vessel wall penetrating catheter of this invention may be used in different ways to accomplish different procedures. Specifically, three general approaches may be employed, namely a) a dual sensor approach wherein one sensor is positioned on the vessel wall penetrating catheter and another sensor is positioned at the target, b) a single sensor approach in a previously sensor-mapped anatomical region and c) a single sensor approach in an anatomical region for which two-dimensional or three-dimensional data has previously been obtained. Each of these approaches is described in more detail herebelow:

A. A Dual Sensor Approach Wherein One Sensor is Positioned on the Vessel Wall Penetrating Catheter and Another Sensor is Positioned at the Target In this embodiment, in addition to the sensor 14 positioned on the vessel wall penetrating catheter 10, a second sensor is positioned at the target location into which the penetrator 20 of the vessel wall penetrating catheter 10 is to extend. Both of these sensors communicate their positions to the computer in real-time (no gating required). The sensor placed at the target location may be mounted on a catheter, such as a mapping catheter, that is advanced transluminally into the target location. This necessarily requires that the target location be a luminal anatomical structure (e.g., a blood vessel) or other anatomical structure having a hollow interior region or a structure within which or on which the second sensor may be placed.

B. A Single Sensor Approach in a Previously Sensor-Mapped Anatomical Region

In this embodiment, a sensor positioned on a mapping catheter is inserted into the anatomical region of interest and the mapping catheter is advanced or moved and the magnetic fields are actuated, so as to provide to the computer with positional data that maps the anatomical structures of interest. Thereafter, after the anatomical structures have been mapped, the mapping catheter may be withdrawn and the vessel wall penetrating catheter 10 having a sensor 14 mounted therein may be inserted. The signals from the sensor 14 of the vessel wall penetrating catheter 10 will then be received by the computer and displayed on a monitor or screen relative to the previously mapped anatomical region. In this manner, the vessel wall penetrating catheter 10 may be positioned and rotationally oriented such that, when the penetrator 20 is subsequently advanced, the penetrator 20 will extend into the desired target location, as shown on the previously mapped anatomical image. Gating may be required if the target location is moving, as would be the case in a beating heart.

C. A Single Sensor Approach in an Anatomical Region for which Two-Dimensional or Three-Dimensional Data has Previously been Obtained In this embodiment, one or more sensors are placed in or on the patient's body, in fixed position(s) relative to the target location. The anatomical region wherein the target location and sensors are placed is then scanned by a scanning apparatus capable of generating two-dimensional or three-dimensional data that is representative of the of tissues and anatomical configuration/structures within the anatomical region of interest (e.g., a tomographic image generated by Magnetic Resonance Imaging (MRI), Computed Axial Tomography (CT), Spiral CT, Electron Beam CT, ultrasound, etc). After the scan has been completed, the patient is positioned within the sensing field (e.g., on a table close to the magnets or external energy field-creating apparatus used to create the magnetic field(s) of other energy field required for the sensing process to be carried out). The vessel wall penetrating catheter 10 having a sensor 14 mounted thereon or therein is inserted and transluminally advanced to the anatomical region of interest. The vessel wall penetrating catheter's sensor 14 is actuated and provides real-time positional and orientation information to the computer so that the exact position and rotational orientation of the vessel wall penetrating catheter 10 may be determined. The other sensors that had been placed on or in the patients body are also actuated such that they also provide real-time data to the computer and the computer uses such sensor data to position the previously scanned image or anatomical data relative to the sensor positions. In some applications, the sensor(s) placed on or in the patient's body may be imageable, or other imageable marker(s) may be placed on or in the body to indicate on the image the location or intended location of each sensor.

Monitor Display

Figure 8:
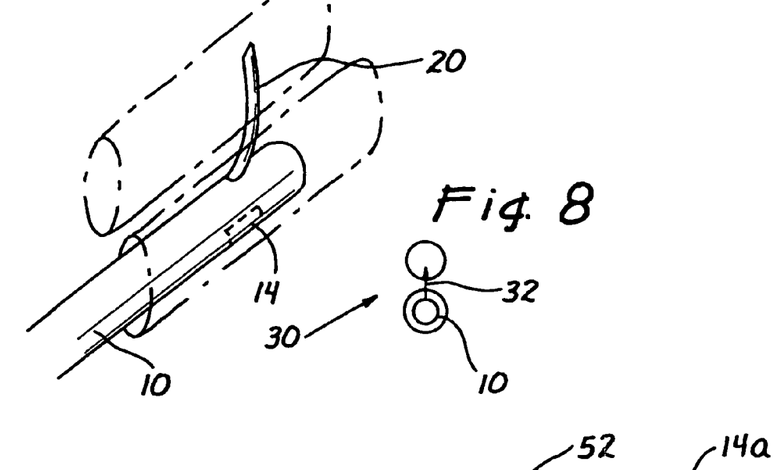
FIG. 8 is a diagram showing one type of visual monitor display that may be provided to permit the operator to visualize the position of a sensor-equipped tissue penetrating catheter during a procedure wherein the penetrating catheter is used to penetrate from the lumen of a first blood vessel to a target location.

FIG. 8 shows an example of a monitor display that may be generated by any of the above-summarized approaches. In the example of FIG. 8, the three-dimensional anatomy of an artery and near-by vein are shown. A sensor-equipped vessel wall penetrating catheter 10 is positioned in the artery. The sensor 14 on the vessel wall penetrating catheter 10 provides three-dimensional data to the computer. The rotational orientation of the vessel wall penetrating catheter 10 is depicted in a two-dimensional screen insert 30 shown in the lower right corner of the display. A pointer 32 and shows the direction in which the penetrator 20 will advance from the vessel wall penetrating catheter 10. While watching the display, the operator may advance and or retract the vessel wall penetrating catheter 10 until its sensor 14 is in the desired longitudinal position. Thereafter, the operator may look at the two-dimensional insert 30 on the display and may rotate the vessel wall penetrating catheter 10 within the artery until the pointer 32 extends into the vein on the two-dimensional display 30. Thereafter, the penetrator 20 may be advanced out of the vessel wall penetrating catheter 10, through the wall of the artery, through any tissues located between the vein and any artery, through the wall of the vein and into the lumen of the vein, at the desired target location. After this initial penetration has been accomplished, various types of additional procedures may be carried out. In some cases, the penetrator 20 will have a guidewire lumen extending therethrough and a guidewire will be passed through the penetrator lumen and into the vein or other target anatomical structure. Thereafter, the penetrator 20 may be retracted, leaving the guidewire in place. A connector, graft, stent, stent graft or other implantable apparatus may then be advanced over the guidewire and positioned as desire. In some applications, such as those where a channel has been created between two blood vessels, a connector may be disposed in the channel and one or more embolic blockers may be placed in the vessel(s) so as to cause blood to flow from one vessel into the other, as in the catheter-based revascularzation procedures (e.g., PICAB™ and/or PICVA™) described in U.S. Pat. No. 5,830,222; 6,068,638; 6,159,225 or 6,071,292 or in co-pending U.S. patent application Ser. Nos. 08/730,324; 09/117,515; 08/837,295; 09/059,532; 08/837,294, 09/056,589; 09/282,276; 09/282,77409/505,149 and/or 09/766,502, the entirety of each such patent and patent application being expressly incorporated herein by reference.

A Percutaneous In Situ Coronary Venous Arterialization (PICVA™) Procedure Performed Using Sensor-Equipped Catheter(s)

Figure 6:
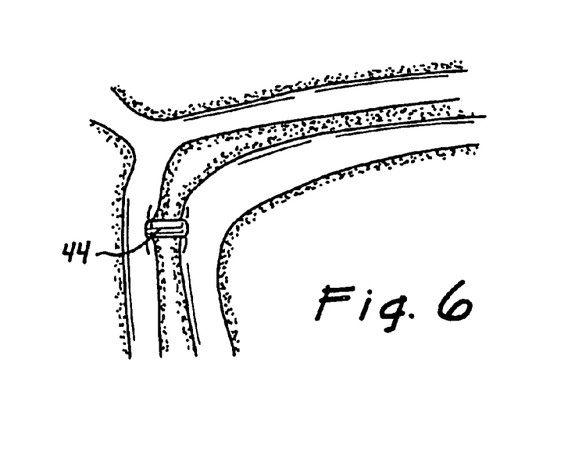
FIG. 6 is a schematic diagram showing a the result of a percutaneous in situ coronary venous arterialization (PICVA™) procedure performed using sensor-equipped catheter(s) of the present invention.
Figure 7:
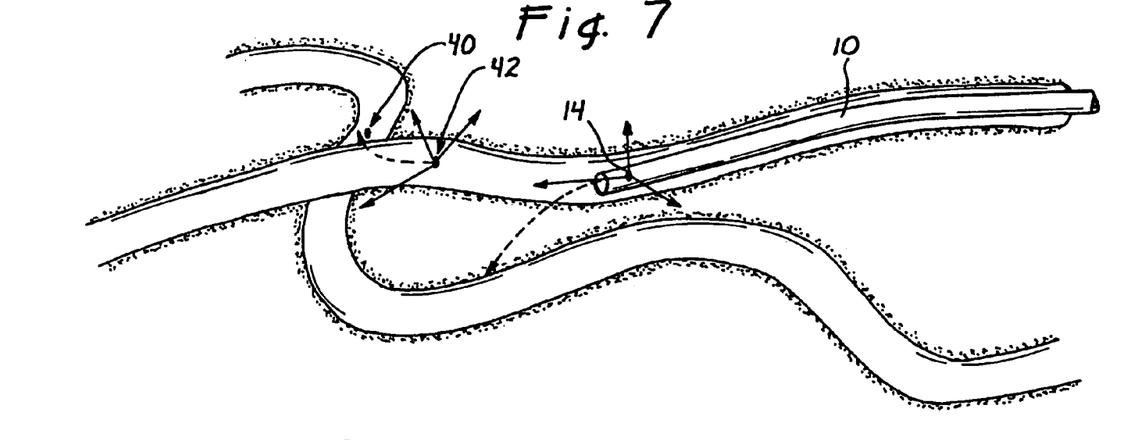
FIG. 7 is a schematic diagram illustrating one way in which the percutaneous in situ coronary venous arterialization (PICVA™) procedure of FIG. 6 may be performed.

FIGS. 6 and 7 show an example of a percutaneous in situ coronary venous arterialization (PICVA™) procedure performed using sensor-equipped catheter(s) of the present invention. In this procedure, vessel 2 has previously been tomographically imaged or has been previously mapped by a sensor-equipped mapping catheter as described hereabove. While the patient is positioned within the sensing field, the sensor-equipped vessel penetrating catheter 10 is advanced into vessel 1 with its sensor 14 actuated, thereby generating a map of the anatomical structure of vessel 1. The computer then compares the anatomical structure of vessel 1 to the anatomical structure of vessel 2 and determines that, in order for the catheter's penetrator 20 to penetrate from the lumen of vessel 1 into the target site 40 located within the lumen of vessel 2, the sensor 14 mounted on the vessel wall penetrating catheter 10 should be positioned at a sensor positioning site 40. Because the sensor 14 is providing real-time positional and rotational data to the operator, the operator is able to advance the vessel wall penetrating catheter 10 through vessel 1 until sensor 14 is positioned at the intended sensor positioning site 42. Thereafter, the operator may rotate the catheter 10 until the rotational orientation of the sensor 14 coincides with the predetermined desired rotational sensor orientation necessary for the penetrator 20 to reach the target location 40. This rotational orientation of catheter 10 may be accomplished with the assistance of the visual rotational orientation display 30 as shown in FIG. 8 and described hereabove. After the vessel wall penetrating catheter 10 has been positioned such that its sensor 14 is at the intended sensor location 42 and the rotational orientation of the sensor 14 is such that the penetrator is precisely aimed at the target location 40, the penetrator 20 will be advanced from the vessel wall penetrating catheter 10, outwardly through the wall of the of vessel 1, through the space between vessel 1 and vessel 2, through the wall of vessel to any into the lumen of vessel to at the target location. Thereafter, a guidewire is advanced through the penetrator 20 and into the lumen of vessel 2 and the penetrator 20 is retracted into the vessel wall penetrating catheter 10. Thereafter, the vessel wall penetrating catheter 10 may be removed from the patient's body. Thereafter, a penetrator tract enlarging apparatus may be advanced over the guidewire and used to dilate or enlarge the tract created by the penetrator 20. Thereafter a connector may be advanced over the guidewire and deployed in to the channel created between vessel 1 and vessel 2 so as to maintain the approximation of the openings formed in vessel 1 and vessel 2 and to facilitate blood flow between vessel 1 and vessel 2. One or more embolic blockers may be positioned in vessel 1 and/or vessel 2 to facilitate the desired blood flow between vessel 1 and vessel 2. The specific types of channel enlarging apparatus, blocker devices, connector devices and the delivery catheters useable for this purpose are described in U.S. Pat. No. 5,830,222; 6,068,638; 6,159,225 or 6,071,292 or in co-pending U.S. patent application Ser. Nos. 08/730,327; 09/117,516; 08/970,694 and 09/056,589, the entireties of which are expressly incorporated herein by reference.

When delivering through catheters some types of the connectors and/or blocker devices used in the PICVA™ procedure described above, as well as other types of radially expandable implantable devices (e.g., stents, stent grafts, etc), it may be desirable to utilize a sensor on such delivery catheter to facilitate the desired positioning and rotational orientation of the delivery catheter before deploying the connector, blocker, stent, stent-graft or other implantable device. FIGS. 9 and 10 show an example of this. In FIGS. 9 and 10, a partially covered connector 50 having open ends and a sidewall opening 52 is placed in a radially collapsed position within a connector delivery catheter 54. A sensor 14a of the type described hereabove is mounted on or in the delivery catheter 54 in a fixed longitudinal position and fixed rotational orientation relative to the rotational orientation of the catheter-mounted connector device 50. In the manner described hereabove with respect to the vessel wall penetrating catheter 10, the precise longitudinal position and rotational orientation of the connector delivery catheter 54 may be determined prior to deployment of the connector 50 from the catheter 54. The ability to precisely determine the rotational orientation of the delivery catheter 54 will allow the side opening 52 of the connector 50 to be pre-positioned before deployment of the connector 50 such that, when the connector 50 is subsequently deployed from the catheter 54 and allowed to radially expand, its side opening 52 will be in the desired location relative to the patient's anatomy. This is specifically illustrated FIG. 10, where a channel has been created between an artery and a vein using a vessel wall penetrating catheter 10, as described hereabove and shown in FIGS. 7, 8 and 11. After the channel has been enlarged, a connector delivery catheter 54 of the type shown in FIG. 9, having a radially collapsed blocker 50 positioned therein, is advanced over the pre-positioned guidewire. The connector delivery catheter 54 is advanced until the longitudinal position of its sensor 14a, as determined by the computer and shown on display, indicates that the connector 50 is positioned within the previously created the vein-artery channel with the opposite ends of the connector 50 disposed in the artery and vein, respectively. Thereafter, the connector delivery Catheter 54 is rotated until the rotational position of the sensor 14a indicates that the side opening 52 of the connector 50 is a pat the desired location. Thereafter, the sheath 56 of the connector delivery catheter 54 is withdrawn in the proximal connection, thereby removing the surrounding constraint from the radially compact connector 50 and allowing the connector 50 to radially expand and become implanted in the position shown in FIG. 10. In such position, some of the arterial blood which enters the end of the connector 50 positioned within the artery may pass-through the side opening 52 and continue to flow through the artery, while the remainder of the arterial blood would diverge through the lumen of the connector 50 and out of its opposite end located within the vein.

Sensor-Equipped Anchorable Sheath

Figure 12:
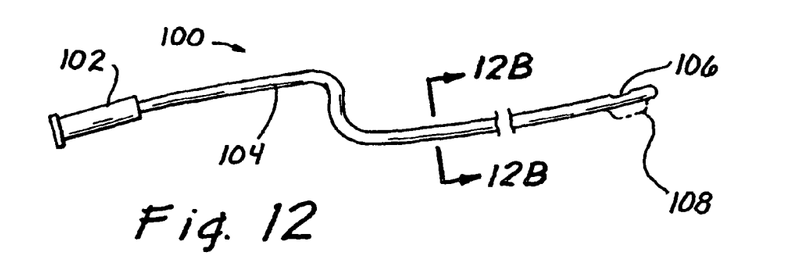
FIG. 12 is a perspective view of a sensor-equipped sheath having an anchorable distal end and a side opening.
Figure 12A:
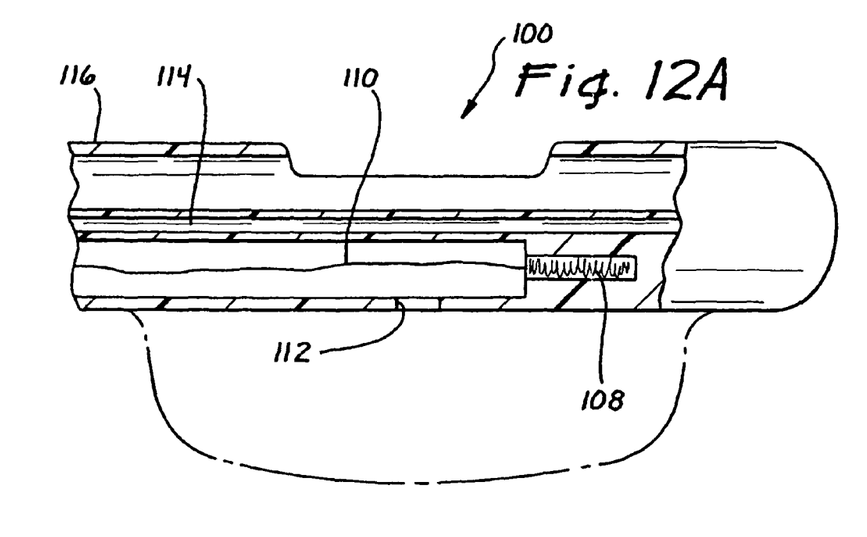
FIG. 12a is an enlarged, partially sectional view of the distal portion of the sensor-equipped sheath of FIG. 12/
Figure 12B:
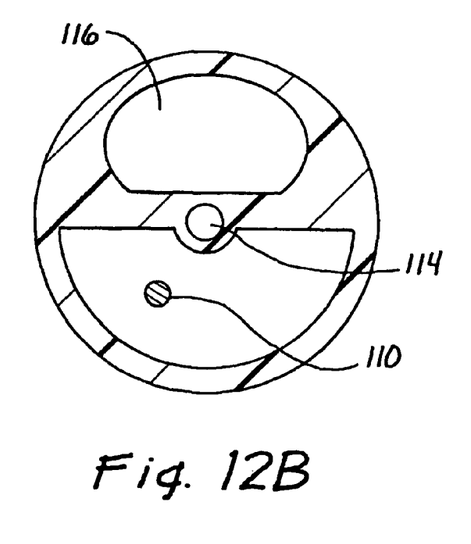
FIG. 12b is a cross sectional view through line 12b-12b of FIG. 12.
Figure 12C:
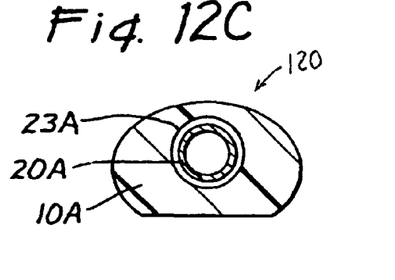
FIG. 12c is a cross sectional view of a non-rotatable tissue penetrating catheter that is insertable into and engageable with the non-round lumen of the sensor-equipped sheath of FIGS. 12, 12a and 12b.

FIGS. 12-12b show an example of a sensor-equipped anchorable sheath 100 of this invention, and FIG. 12c shown a cross section of a specially designed penetrating catheter that is useable in conjunction with the sensor-equipped anchorable sheath 100.

The sheath 100 comprises a handpiece or hub 102 and an elongate, flexible sheath body 104 having a side aperture 106 formed in its side wall near its distal end. An anchoring balloon 108 is positioned on the side wall of the sheath, 100 diametrically opposite its side aperture 106. At least one sensor 108 is mounted in the distal portion of the sheath body 104 and a wire 110 extends through a blind lumen 112 to connect the sensor to the extracorporeal sensing and control equipment described elsewhere in this application. It will be appreciated that, alternatively to the single sensor embodiment shown, two or more sensors 108 may be positioned at two or more locations in or on the sheath body 104. A guidewire lumen 114 extends longitudinally through the sheath 100 to permit it to be advanced over a guidewire in accordance with well known and established operational technique. A working lumen 116 extends through the sheath body 104 at least to the location of the side aperture 106 such that a separate catheter, such as a tissue penetrating catheter 120 (FIG. 12c) may be advanced into the working lumen 116 to a position adjacent to the side aperture 106. The working lumen is non-round in cross section, keyed, serrated or otherwise configured such that when the catheter 120 is inserted into the working lumen 116 the catheter 120 will not rotate.

In one mode of operation, the sensor-equipped sheath may be inserted and advanced through the vasculature to a position that is near or adjacent to a target location (e.g., a location within the lumen of another blood vessel, a location within tissue, an anatomical structure, a tumor, etc.). In the manner described above, the sensor 108 may be used to longitudinally and rotationally position the sheath such that its side aperture 106 is directed at and aligned with the target location. The anchoring balloon 108 is then inflated to anchor the sheath body 104 in fixed longitudinal and rotational position within the vessel. Thereafter, a catheter or elongate device, such as a penetrating catheter 120 is inserted into the working lumen 116 in a known rotational orientation. The catheter 120 is then advanced to a position where its penetrator outlet port (not shown in FIG. 12c) is within the side aperture 106. The penetrator 20a may then be advanced through the side aperture 106 and to the target location. In this manner, the sheath 100 is used to guide the specific position and orientation of the penetrating catheter 120, and the penetrating catheter is non-rotatably advanced through the working lumen 116 of the sheath such that the penetrating catheter 120 must remain in fixed rotational orientation relative to that of the pre-positioned and anchored sheath body 104.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, it is to be understood and appreciated that the magnetic sensors and related apparatus described above may be replaced with or interchanged with other types of sensors and sensing apparatus (e.g., radiofrequency, other magnetic sensors, ultrasound, microwave, light, x-ray, etc) that are useable for the intended purpose. All such reasonable additions, deletions, modifications and alterations are to be considered equivalents of the described examples and embodiments and are to be included within the scope of the following claims.

What is claimed is:

1. A method for using a navigable tissue penetrating catheter system in a human or veterinary patient to penetrate from a location within the lumen of an artery or vein, outwardly through the wall of that artery or vein and to a target location outside of that artery or vein, said method comprising the steps of:
    (A) providing a navigable tissue penetrating catheter system comprising;
        i) a field generator for generating a sensing field about at least a portion of the body of a human or veterinary patient;
        ii) a tissue penetrating catheter comprising a catheter body, a penetrator that is advanceable laterally from the catheter body so as to penetrate outwardly through the wall of an artery or vein in which the catheter body is positioned to a target location and a sensor mounted on or in the catheter body for sensing components of the sensing field and emitting signals indicative of the rotational orientation of the sensor within the sensing field; and
        iii) a sensor-monitor adapted to receive signals from the sensor and to provide, on the basis of those signals, indicia of the rotational orientation of the sensor within the sending field;
    (B) providing a sensor-equipped mapping catheter;
    (C) using the sensor equipped mapping catheter to map or mark the target location;
    (D) using the field generator to create a sensing field;
    (E) positioning at least the portion of the patient's body in which the target location is located within the sensing field;
    (F) inserting the tissue penetrating catheter into the patient's body and advancing the catheter into the lumen of an artery or vein located within the sensing field;
    (G) actuating the sensor of the tissue penetrating catheter such that signals from the sensor are received by the sensor monitor;
    (H) using the indicia provided by the sensor monitor to rotationally orient that catheter body within the anatomical conduit such that, when the penetrator is subsequently advanced laterally from the catheter body, it will penetrate outwardly through the wall of the anatomical conduit in which the catheter body is positioned and to the target location outside of the artery or vein in which the tissue penetrating catheter is positioned; and
    (I) advancing the penetrator from the catheter body, through the wall of the artery or vein in which the catheter body is positioned and to the target location.

2. A method according to claim 1 wherein the target location is selected from the group consisting of:
    an artery other than one in which the tissue penetrating catheter is positioned;
    a vein other than one in which the tissue penetrating catheter is positioned;
    a location within the parenchyma of an organ;
    a cavity within an organ;
    a body cavity;
    an aberrant anatomical structure
    an anatomical malformation;
    a location to which a drug, substance, flow of energy or apparatus is to be delivered; and
    a location from which a sample, reading image or diagnostic information is to be obtained.

3. A method according to claim 1 further comprising the steps of:
- positioning a body-mounted sensor in or on the patient's body in a known positional relationship to an anatomical landmark,
- obtaining a three dimensional scan of at least the portion of the patients body in which the body-mounted sensor and the target location are located;
- displaying the three dimensional scan to the operator; and
- actuating the body-mounted sensor during performance of Steps F-G of the method, thereby enabling the operator to discern the position the body-mounted sensor and to ascertain the position of the target location within the sensing field on the basis of the previously obtained three dimensional scan.

4. A method according to claim 1 further comprising the step of:
- displaying the map of the target location to the operator.

5. A method according to claim 4 wherein the map of the target location is displayed by the sensor monitor along with the indicia received from the sensor of the tissue penetrating catheter.

* * * * *